US008435956B2

(12) United States Patent
Thomas

(10) Patent No.: US 8,435,956 B2
(45) Date of Patent: May 7, 2013

(54) COMPOSITIONS AND METHODS FOR PROTECTING CELLS FROM TOXIC EXPOSURES

(75) Inventor: James P. Thomas, New Albany, OH (US)

(73) Assignee: Percitus Biosciences, LLC, Madison, WI (US)

(*) Notice: Subject to any disclaimer, the term of this patent is extended or adjusted under 35 U.S.C. 154(b) by 0 days.

(21) Appl. No.: 13/469,984

(22) Filed: May 11, 2012

(65) Prior Publication Data
US 2012/0252764 A1  Oct. 4, 2012

Related U.S. Application Data

(63) Continuation of application No. 12/057,097, filed on Mar. 27, 2008, now abandoned.

(60) Provisional application No. 60/920,176, filed on Mar. 27, 2007.

(51) Int. Cl.
A61K 38/05  (2006.01)

(52) U.S. Cl.
USPC .......... 514/21.91; 530/332; 530/336; 514/19.2

(58) Field of Classification Search .................. None
See application file for complete search history.

(56) References Cited

U.S. PATENT DOCUMENTS

| 4,927,808 | A | 5/1990 | Kitahara et al. |
| 5,624,955 | A | 4/1997 | Nagasawa et al. |
| 5,661,188 | A | 8/1997 | Weissman |
| 5,994,409 | A | 11/1999 | Stogniew |
| 6,384,259 | B1 | 5/2002 | Stogniew |
| 6,407,278 | B2 | 6/2002 | Stogniew |
| 6,462,017 | B1 | 10/2002 | Rudolph |
| 6,573,253 | B2 | 6/2003 | Stogniew et al. |
| 6,696,483 | B2 | 2/2004 | Singh |
| 6,753,323 | B2 | 6/2004 | Stogniew |
| 6,841,545 | B2 | 1/2005 | Stogniew |
| 7,151,094 | B2 | 12/2006 | Stogniew |
| 2004/0198841 | A1 | 10/2004 | Neuwelt |

FOREIGN PATENT DOCUMENTS

WO   2005/074903   8/2005

OTHER PUBLICATIONS

Cascinu et al., Neuroprotective Effect of Reduced Glutathione on Oxaliplatin-Based Chemotherapy in Advanced Colorectal Cancer: A Randomized, Double-Blind, Placebo-Controlled Trial, Journal of Clinical Oncology, vol. 20, Issue 16 (Aug.), 2002: 3478-3483.
Moscow and Dixon, "Glutathione-related enzymes, glutathione and multidrug resistance" 1993, Cytotech. 12:155-70.
Brizel et al., Phase III Randomized Trial of Amifostine as a Radioprotector in head and neck Cancer, 2000, J. Clin. Onc. 18:3339-45.

Antonadou et al., Randomized Phase III Trial of Radiation Treatment ± Amifostine in Patients with Advanced-Stage Lung Cancer, 2001, Int. J. Rad. Onc. Biol. Phys. 51:915-22.
Yuhas, "Radiotherapy of experimental lung tumors in the presence and absence of a radioprotective drug, S-2-(3-aminopropylamino)ethylphosphorothioic acid (WR-2721)" 1973, J. Natl. Cancer Inst. 50:69-78.
Physician's Desk Reference, Goodman and Gilman's "Pharmaceutical Basis of Therapeutics" 10th Edition, Eds. Hardman et al., 2002.
DeVita et al., "Biologic Therapy of Cancer", 2nd Edition, 1995, JB Lippincott Co. Publ, p. 919.
Tietze F: "Enzymic Method for Quantitative Determination of Nanogram Amounts of Total and Oxidized Glutathione Applications to Mammalian Blood and Other Tissues" Analytical Biochemistry, 27(3): 502-522 (1969).
International Search Report of co-pending international application No. PCT/US2008/058468 dated Jun. 30, 2008.
Binkley, "Preparation and Properties of S-phosphocysteine" J. Biol. Chem., 1952, 195,283-5.
Hospers et al. ("The sulfhydryl containing compounds WR-2721 and glutathione as radio- and chemoprotective agents," Brit. J. Cancer, 1999, 80, 629-38).
Levy et al. ("Transport of glutathione diethyl ester into human cells," Proc. Natl. Acad. Sci. USA, 1993, 90, 9171-9175).
Bastin et al. ("Salt Selection and Optimisation Procedures for Pharmaceutical New Chemical Entities," Organic Process Res. & Dev, 2000, 4, 427-35).
Block, K., et al., "Commentary: The Pharmacological Antioxidant Amifostine—Implications of Recent Research for Integrative Cancer Care," Integrative Cancer Therapies, vol. 4, No. 4, 2005, pp. 329-351.
Brizel, D.M., et al., "Phase III Randomized Trial of Amifostine as a Raadioprotector in Head and Neck Cancer," Journal of Clinical Oncology, vol. 18, No. 19, Oct. 1, 2000, pp. 3339-3345.
Cetingul, N., et al., "Cytoprotective Effects of Amifostine in the Treatment of Childhood Malignancies," Pediatr Blood Cancer, 2009, vol. 52, pp. 829-833.
Joshi, G., et al., "Glutathione Elevation by y-Glutamyl Cysteine Ethyl Ester as a Potential Therapeutic Strategy for Preventing Oxidative Stress in Brain Mediated by In Vivo Administration of Adriamycin: Implication for Chemobrain," Journal of Neuroscience Research, 2007, vol. 85, pp. 497-503.
Koukourakis, M., et al., "Amifostine before Chemotherapy: Improved Tolerance Profile of the Subcutaneous Over the Intravenous Route," Clinical Cancer Research, Aug. 15, 2003, vol. 9., 3288-3293.
Omenn, G., "Chemoprevention of lung cancers: lessons from CARET, the beta-carotene and retinol efficacy trial, and prospects for the future," European Journal of Cancer Prevention, 2007, vol. 16, pp. 184-191.
Thorstad, W., et al., "Toxicity and Compliance of Subcutaneous Amifostine in Patients Undergoing Postoperative Intensity-Modulated Radiation Therapy for Head and Neck Cancer," Semin Oncol 31, Suppl. 18, pp. 8-12.
Yuhas, J.M., et al., "On the Potential Application of Radioprotective Drugs in Solid Tumor Radiotherapy," Radiation-Drug Interactions in the Treatment of Cancer, 1980, pp. 113-135.

Primary Examiner — Christina Bradley
(74) Attorney, Agent, or Firm — Foley & Lardner, LLP

(57) ABSTRACT

The present invention provides compositions and methods for protecting cells and tissues from damage associated with therapeutic treatments of cancers and other diseases and conditions where reactive oxygen species are produced. The present invention also provides compositions useful as research reagents.

18 Claims, 1 Drawing Sheet

UNITED STATES PATENT AND TRADEMARK OFFICE
CERTIFICATE OF CORRECTION

PATENT NO. : 8,435,956 B2
APPLICATION NO. : 13/469984
DATED : May 7, 2013
INVENTOR(S) : James P. Thomas It is certified that error appears in the above-identified patent and that said Letters Patent is hereby corrected as shown below:

ON THE TITLE PAGE

(73) Assignee: "Percitus" should read as Perscitus

Signed and Sealed this
Nineteenth Day of November, 2013

Teresa Stanek Rea
*Deputy Director of the United States Patent and Trademark Office*

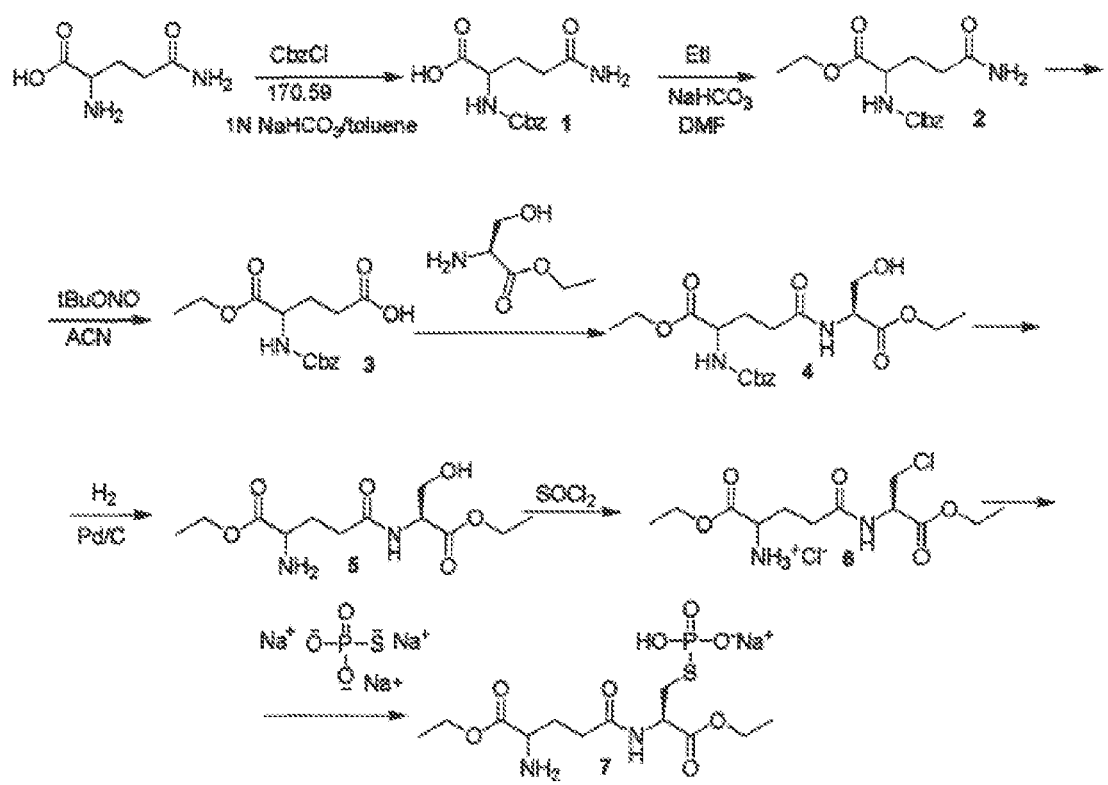

COMPOSITIONS AND METHODS FOR PROTECTING CELLS FROM TOXIC EXPOSURES

The present application is a continuation of U.S. patent application Ser. No. 12/057,097, filed Mar. 27, 2008, which claims priority to expired U.S. Provisional Patent Application Ser. No. 60/920,176, filed Mar. 27, 2007, each of which are herein incorporated by reference in its entirety.

FIELD OF THE INVENTION

The present invention provides compositions and methods for protecting cells and tissues from damage associated with therapeutic treatments of cancers and other diseases and conditions where reactive oxygen species are produced. The present invention also provides compositions useful as research reagents.

BACKGROUND OF THE INVENTION

Cancers are a leading cause of death in animals and humans. The leading cancer therapies today are surgery, radiation and chemotherapy. In spite of advances in the field of cancer treatment, each of these known therapies has serious side effects. For example, surgery disfigures the patient or interferes with normal bodily functions. Chemotherapy or radiation therapies cause patients to experience acute debilitating symptoms including nausea, vomiting, diarrhea, hypersensitivity to light, hair loss, etc. The side effects of these cytotoxic compounds frequently limit the frequency and dosage at which they can be administered. The main reason chemotherapy is so debilitating and the symptoms so severe is that chemotherapeutic drugs are often unable to differentiate between normal, healthy cells and the tumor cells they are designed to target. Therefore, as they target tumor cells they also target healthy cells thereby causing the toxic side effects to the subject receiving the chemotherapy. As well, radiation therapy targets the whole system, not just tumor cells, so side effects are once again severe for the subject receiving radiation therapy.

While chemotherapeutic compounds have been found to be effective and are in general clinical use as anti-proliferative agents, there are well recognized drawbacks associated with their administration. Chemotherapeutic alkylating agents have marked cytotoxic action and the ability of these drugs to interfere with normal mitosis and cell division can be lethal. Chemotherapeutic antimetabolites can lead to anorexia, progressive weight loss, depression, and coma. Prolonged administration of antimetabolites can result in serious changes in bone marrow. Both the alkylating agents and the antimetabolities generally have a depressive effect on the immunosuppressive system. Prolonged administration of natural products such as vinca alkyloids can also result in bone marrow depression. Hydroxy urea and other chemically derived chemotherapeutic agents can lead to rapid reduction in levels of adrenocorticosteroids and their metabolites. The administration of hormonal chemotherapeutic compounds or radioactive isotopes is also undesirable from the viewpoint of inflicting damage on the immunosuppressive system and thereby disabling the body's defenses against common infections. Moreover, it is recently reported that cognitive function is compromised upon administration of some chemotherapeutic compounds, in particular the administration of adriamycin in treating breast cancer. Such cognitive dysfunction is loosely termed "chemo brain", and is marked by increased oxidative stress and cellular apoptosis in the brain (Joshi et al., 2007, J. Neurosci. Res. 85:497-503).

Glutathione (GSH) represents one of the most prevalent organic molecules within the cell, with concentrations ranging from 0.1 to 15 mM. Glutathione functions primarily as an antioxidant, reacting with toxic species as well as serving as a cofactor for a number of protective enzymes such as glutathione peroxidase and glutathione transferase. Glutathione is also an important determinant of the cell's ability to pump toxic substances, such as chemotherapeutic drug metabolites, out of the cell. The concentration of glutathione and the extent of glutathione oxidation are thought to be a key determinant of cells undergoing programmed cell death (apoptosis) in response to chemotherapy or radiation therapy.

Several sulfhydryl containing compounds have been developed to protect normal tissues from the toxic effects of either chemotherapy or radiation therapy. For example, glutathione has been utilized in clinical trials to protect against the toxic effects of chemotherapy. Cascinu et al. (2002, J. Clin. One. 20:3478-83) found that co-administration of reduced glutathione could significantly reduce the neuropathy seen with the chemotherapeutic drug oxaliplatin. However, the effect of reduced glutathione is relatively limited in that this compound is rapidly hydrolyzed when given intravenously. Unfortunately, systemically administered glutathione protects tumor cells and normal cells equally and has not been shown to improve the therapeutic index. Also, elevation in glutathione levels is a common characteristic of tumor cells resistant to chemotherapy (Moscow and Dixon, 1993, Cytotech. 12:155-70).

Sodium 2-mercaptoethane sulphonate (Mesna) is a thiol-producing compound that is used in clinical oncology to prevent bladder damage from high doses of chemotherapeutic alkylating agents (e.g., cyclophosphamide, cisplatin, ifosfamide, carboplatin, doxorubicin and its derivatives, mitomycin and its derivatives). Mesna (UROMITEXAN, MESNEX; U.S. Pat. Nos. 5,661,188, 6,696,483 and 6,462,017) is excreted rapidly in the urine which limits its general utility except for bladder protection.

Amifostine (ETHYOL, WR-2721; U.S. Pat. Nos. 7,151,094, 6,841,545, 6,753,323, 6,407,278, 6,384,259, 5,994,409) was developed as a radiation protection agent by the U.S. Walter Reed Army Institute of Research in the 1950s. Amifostine (S-2-(3-aminopropylamino)ethylphosphorothioic acid) is a cytoprotective adjuvant used in cancer chemotherapy involving DNA-binding chemotherapeutic agents and is used therapeutically to reduce the incidence of fever and infection induced by DNA-binding chemotherapeutic agents including alkylating agents (e.g. cyclophosphamide) and platinum-containing agents (e.g. cisplatin). It is also used to decrease the cumulative nephrotoxicity associated with platinum-containing agents and is indicated to reduce the incidence of dry mouth in patients undergoing radiotherapy for head and neck cancer. Amifostine is an organic thiophosphate prodrug that is dephosphorylated in vivo by alkaline phosphatase (e.g., alkaline phosphatase is capable of hydrolyzing phosphorothioates in addition to phosphoether moieties in a variety of compounds) to the active cytoprotective thiol metabolite (WR-1065). The selective protection of non-malignant tissues is believed to be due to higher alkaline phosphatase activity, higher pH, and vascular permeation of normal tissues; dephosphorylation takes place preferentially in normal blood vessels but to a much lesser extent in tumor vessels because tumors are more acidic and the newly formed tumor blood vessels do not significantly express the enzyme alkaline phosphatase. In randomized Phase III human trials, amifostine has been shown to reduce toxicity with 1) chemotherapy and radiation therapy in head and neck cancer (David et al., 2000, J. Clin. One. 18:3339-45); 2) radiation therapy in lung cancer patients (Antonadou et al., 2001, Int. J. Rad. One. Biol. Phys. 51:915-22); 3) myelosuppression from carboplatin; and 4) chemotherapy and radiation therapy in rectal cancer. Amifostine was originally indicated to reduce the cumulative renal toxicity from cisplatin in non-small cell lung cancer. However, while nephroprotection was observed, the fact that amifostine could protect tumors could not be excluded. Therefore, given better treatment options for non-small cell lung cancer, amifostine's indication for non-small cell lung cancer was withdrawn in 2005.

As such, what are needed are novel compositions for use as broad-spectrum chemoprotectants and radioprotectants. Such novel compositions would not only serve as adjuvants to chemo and radiation therapies to protect the subjects normal cells from the toxicity associated with such therapies, but such novel compositions would also prove useful as research reagents in the study of, for example, chemotherapeutics and cellular biology.

SUMMARY OF THE INVENTION

The present invention provides compositions and methods for protecting cells and tissues from damage associated with therapeutic treatments of cancers and other diseases and conditions where reactive oxygen species are produced. The present invention also provides compositions useful as research reagents.

In one embodiment, the compositions of the present invention are used in conjunction with cytotoxic chemotherapy and/or radiation therapy in the treatment of subjects, and are broadly applicable to such treatment regimens. It is contemplated that by decreasing toxicity to normal cells, the compositions thereby allow for the escalation (e.g., high dose, prolonged treatment, use of drugs otherwise considered too toxic, etc.) of chemotherapy or radiation dosing, resulting in more effective treatments. Likewise, the compounds find use in conjunction with existing therapeutic protocols to reduce toxicity and the associated underlying sign, symptoms, and side effects.

In some embodiments, the compositions and methods of the present invention find utility in protecting normal cells from toxicity due to treatment regimens associated with cellular toxicity due to, for example, AIDS, anti-fungal therapy, antibacterial therapy, and intravenous contrast agents. The compositions and methods can also be used to treat disorders that are induced by aging and metabolic disorders, including, but not limited to diabetes.

The present invention provides compositions and methods for the treatment of a wide variety of metabolic processes and disorders wherein free radicals, and therefore cell damage or apoptosis, can occur. The methods of the present invention are also suitable for the treatment of disorders relating to basal metabolism such as heat production of an individual at the lowest level of cell chemistry in the waking state, or the minimal amount of cell activity associated with the continuous organic functions of respiration, circulation and secretion; carbohydrate metabolism such as the changes that carbohydrates undergo in the tissues, including oxidation, breakdown, and synthesis; electrolyte metabolism such as the changes which the various essential minerals, sodium, potassium, calcium magnesium, etc. undergo in the fluids and tissues of the body; fat metabolism such as the chemical changes, oxidation, decomposition, and synthesis, that fats undergo in the tissues; protein metabolism such as the chemical changes, decompositions, and synthesis that protein undergoes in the tissues; and respiratory metabolism such as the exchange of respiratory gases in the lungs and the oxidation of foodstuffs in the tissues with the production of carbon dioxide and water.

In one embodiment, the present invention provides compositions and methods for protecting tissues and cells from damage caused by any therapy to a subject that is toxic to normal cells (e.g., non-diseased cells such as non-cancerous cells), for example chemotherapy or radiation therapy. In some embodiments, the present invention inhibits or decreases apoptosis in normal cells and tissues due to therapies such as, for example, chemotherapy and radiation therapy.

In one embodiment, the compositions of the present invention provide research reagents for the scientific community for use in experimental methods. In some embodiments, the compositions are used in in vitro assays. In some embodiments, the compositions are used in in vivo assays.

The present invention relates, in part, to compositions and methods for treating cellular toxicities associated with the administration to a subject of one or more therapeutic agents, which comprise administering a therapeutically effective amount of one or more compositions of the present invention, or pharmaceutically acceptable salts thereof, to the subject receiving said one or more therapeutic agents.

In some embodiments, the therapeutic agent utilized is one that permits regioselective increase of the concentration of a natural, non-toxic, protective material in healthy tissue. Preferably, said compound is not increased, or increased to a lesser extent, in a cell that is targeted for killing (e.g., a cancer cell). For example, in some embodiments, the therapeutic agent provides a regioselective increase in the concentration of glutathione in healthy tissue. Examples of therapeutic agents that produce this effect are shown in Formula I, II, and III. The present invention is not limited to these specific compounds. In some embodiments, the therapeutic agent is a protected glutathione molecule that can undergo a selective deprotection process (e.g., a two-step deprotection process) that locally increases the concentration of deprotected glutathione in cells of interest (e.g., healthy tissue). In some embodiments designed to provide glutathione to cells of interest, the therapeutic agent involves carboxyl group protection. In some embodiments, one of the carboxyl groups of glutathione is protected. In some embodiments, both carboxyl groups of glutathione are protected. In some embodiments, a phosphorothioate derivative of glutathione is provided, including mono- and di-ethyl esters thereof. In some embodiments, one or more methyl or ethyl groups are used to protect one or more carboxyl groups of a glutathione molecule (see e.g., Formula I, II, and III). In some embodiments, any protecting group that can be cleaved (e.g., by a cellular esterase) is employed. Preferably, the product of the cleavage is minimally toxic or non-toxic. Preferably, the product is natural glutathione or a functionally equivalent derivative thereof. In some embodiments, the protecting group is a polyethylene glycol (PEG). In some embodiments, the protecting group is any organic moiety that facilitates membrane permeability, including short peptide or other materials useful for facilitating drug delivery.

The present invention is not limited to the use of glutathione as a protective agent. In some embodiments, the therapeutic agent is any protective agent that, alone or in combination with other agents, when modified in vivo in a regioselective manner, provides a free-radical scavenger in the desired target cell. For example, the therapeutic agent may comprise alpha-lipoic acid comprising a phosphate protecting group or other protecting group (e.g., PEG) protecting the carboxyl group. A variety of compounds may be employed that can undergo regioselective deprotection to provide intracellular protective compounds.

In some embodiments, the therapeutic agent is provided as part of a bioconjugate or complex. For example, in some embodiments, the therapeutic agent is provided in, on, or with a nanoparticle, liposome, micelle, dendrimer, or other biocompatible material or biopolymer (e.g., carbohydrate) useful as a drug carrier.

In one embodiment, the present invention relates to compositions and methods for treating cellular toxicities associated with administration of a chemotherapeutic agent or other toxic agent wherein a composition comprising Formula I, II, or III, other compounds described herein, or salts, metabolites, functional derivatives, functional analogues, esters and pro-drugs thereof, are administered prior to, with, and/or after administration of the chemotherapeutic agent, or alternatively, at the first indication of toxicity caused by the chemotherapeutic agent(s). Toxicity is caused by, for example, those compounds as listed in Table 1.

The present invention further relates to methods for treating cellular toxicities associated with the administration of therapeutic agents by administering a composition comprising Formula I, II, or III, other compounds described herein, or salts, metabolites, functional derivatives, functional analogues, esters and pro-drugs thereof after clinical appearance of toxicities following therapeutic treatment. In some embodiments, the invention relates to methods of treating toxicities associated with the exposure of a subject to radiation therapy, which comprise administering to the subject a therapeutically effective amount of one or more of the compositions as described herein, or a pharmaceutically acceptable salt thereof, concurrent with, or after the occurrence of, radiation therapy. In one embodiment, the present invention relates to compositions and methods for treating cellular toxicities associated with administration of a radiation therapy regimen wherein a composition comprising Formula I, II, or III, other compounds described herein, or salts, metabolites, functional derivatives, functional analogues, esters and pro-drugs thereof, are administered prior to, with, and/or after administration of the radiation therapy, or alternatively, at the first indication of toxicity caused by the radiation therapy.

In one embodiment, the present invention provides a composition comprising Formula I. In some embodiments, Formula I comprises $R_1$ and $R_2$ groups that are each independently ethyl or methyl groups. In some embodiments, the present invention provides a composition comprising Formula I wherein n is 2. In some embodiments, the present invention provides a composition comprising Formula I wherein $R_1$ and $R_2$ groups that are ethyl groups and n is 2. In some embodiments, Formula I comprises a monosodium salt of the phosphorothioate group.

In one embodiment, the present invention provides a composition comprising (S)-ethyl 2-amino-5-((R)-1-ethoxy-1-oxo-3-(phosphonothio)propan-2-ylamino)-5-oxopentanoate monosodium salt.

In one embodiment, the present invention provides a method for protecting cells from the toxic effects of free radical generating therapies comprising providing a subject with a conditions being treated with therapies that are toxic to normal cells and disease cells, and co-administering to said subject a composition comprising Formula I and a therapy that is toxic to said normal cells and disease cells.

In one embodiment, the present invention provides a method of treating subjects with cancer comprising providing a subject with cancer and co-administering to said subject a treatment regimen comprising Formula I and a chemotherapy drug and/or radiation therapy.

DESCRIPTION OF THE FIGURES

FIG. 1 depicts a synthesis method of (S)-ethyl 2-amino-5-(R)-1-ethoxy-1-oxo-3-(phosphonothio)propan-2-ylamino)-5-oxopentanoate monosodium salt an embodiment of the invention, as described in Example 1.

DEFINITIONS

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "co-administration" refers to the administration of both a composition of the present invention with another type of therapy, for example chemotherapy or radiation therapy. Co-administration can be at the same time in the same administrative form (e.g., injection, pill, liquid), or co-administration can be two compositions given at the same time, but not in the same administrative form.

As used herein, the term "reactive oxygen species" refers to highly reactive chemicals, containing oxygen, that react easily with other molecules, resulting in potentially damaging modifications. Reactive oxygen species include, for example, oxygen ions, free radicals and peroxides both inorganic and organic such as hydrogen peroxide, superoxide, hydroxyl radical, lipid hydroperoxidase and singlet oxygen. They are generally very small molecules and are highly reactive due to the presence of unpaired valence shell electrons.

As used herein, "toxic effects" refers to damaging modifications to cells and tissues caused by reactive oxygen species. For example, a toxic effect of a reactive oxygen species is a cell that is modified to undergo apoptosis.

As used herein, "free radical generating therapies" refers to drugs, chemicals, small molecules, peptides, radiation, and other such therapies that are applied to subjects, either alone or in combination, to treat a disorder or disease, wherein such a therapy results in the generation of free radicals in both non-diseased and diseased cells and tissues.

DETAILED DESCRIPTION OF THE INVENTION

Certain illustrative embodiments of the invention are described below. The present invention is not limited to these embodiments.

The compositions of the present invention provide novel chemoprotectants that, when administered to a subject receiving chemo or radiation therapy, selectively protects the subject's cells and tissues, and not tumor tissues, from toxic therapeutic effects. Once activated, compositions of the present invention serve, for example, as a direct precursor to glutathione, a key regulator of apoptosis. The presence of a phosphorothioate moiety, or other protecting moiety, in the compositions as described herein requires cleavage by alkaline phosphatase, present in normal cells but much less so in tumor neovasculature. Elevations of glutathione in normal tissues render the patient less susceptible to the toxic effects of chemotherapy and radiation therapy, whereas cancerous cells within a tumor are not so protected.

In some embodiments, the compositions as described herein undergo dephosphorylation (e.g., by alkaline phosphatase) in vitro under experimental parameters or in vivo in the normal cells and tissues of a subject. Once dephosphorylated, the composition comprises an active free sulfhydryl (thiol, —SH) group that protects against the toxicities associated with chemotherapy and radiation therapy by acting as a scavenger for reactive oxygen species created by such therapies (Yuhas, 1977, in: *Radiation-Drug Interactions in Cancer Management*, pp. 303-352); Yuhas, 1973, J. Natl. Cancer Inst. 50:69-78; incorporated by reference herein in their entireties).

In one embodiment, the present invention relates to protection of non-diseased cells and tissues by administering prior to, during, or after, irradiation and/or chemotherapy to a tumor tissue, a therapeutically effective amount of a composition as described herein. In some embodiments, the administration of a composition of the present invention is directed specifically to the non-diseased cells and tissues, whereas the administration of the chemotherapy and/or irradiation is not so discriminating.

In one embodiment, the compositions of the present invention include small molecules, or analogs thereof, of the structure as seen in Formula I:

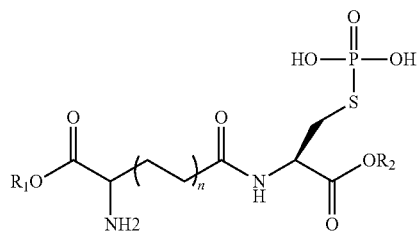

wherein:
$R_1$ and $R_2$ are each, separately, hydrogen, methyl, or ethyl; and
n is an integer from 2 to 10.

In one embodiment, the present invention provides salts, solvates and hydrates of the compounds as described herein. An example of an acceptable salt is found in Formula II:

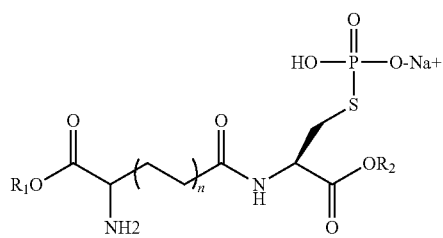

wherein:
$R_1$ and $R_2$ are each, separately, hydrogen, methyl, or ethyl; and
n is an integer from 2 to 10.

In some embodiments, a further example of a salt composition suitable for use as a composition in the methods of the present application is found in Formula III:

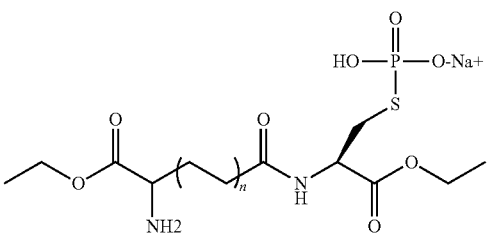

wherein n is an integer from 2 to 10.

In some embodiments, two or more therapeutic molecules of interest are provided in a single therapeutic agent as a single molecule, such that the two or more therapeutic molecules of interest are generated intracellularly. One or more of the constituents may also be selected to increase molecule stability, cell permeability, or other desired properties. For example, in one embodiment, the compositions of the present invention include small molecules, or analogs thereof, of the structure as seen in Formula IV:

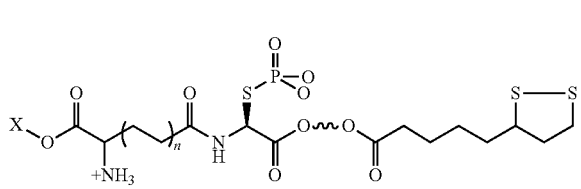

∿∿∿ = esterase cleavable linker
X = lipoic acid, Me, Et, or H

The compound of Formula IV is metabolized to provide both glutathione and lipoic acid to a cell, each providing protection against toxic agents or conditions. Such a molecule undergoes, for example, cleavage of the thiol protecting phosphate by alkaline phosphatase. It is contemplated that the nonpolar molecule is readily cell permeable. Esterase cleavage of the conjugate and liberation of the glutathione molecule and alpha-lipoic acid provide intracellular protection.

Therapeutic agents can also be provided as dimers or other multimers of protective molecules. For example, in some embodiments, the therapeutic agent comprises a molecule as seen in Formula V, a protected dimer of glutathione:

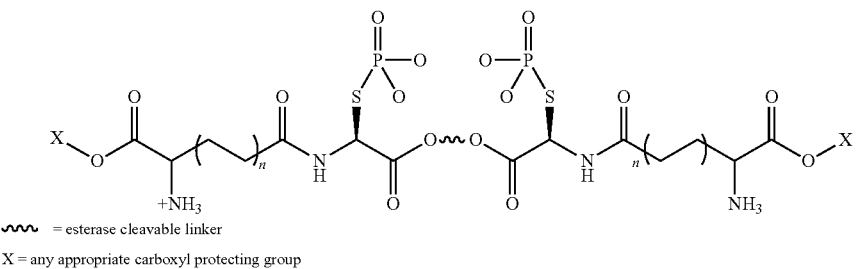

∿∿ = esterase cleavable linker
X = any appropriate carboxyl protecting group

In some embodiments, compositions of the present invention are co-administered with chemotherapy and/or anticancer therapy and/or radiation therapy and another chemoprotectant compound (e.g., amifostine, mesna). In some embodiments, the administration of a composition of the present invention is directed specifically to the non-diseased cells and tissues, whereas the administration of the chemotherapy and/or irradiation is not so discriminating.

For example, Table 1 lists compounds for co-administration with a composition of the present invention.

TABLE 1

| | | |
|---|---|---|
| Aldesleukin (des-alanyl-1, serine-125 human interleukin-2) | Proleukin ® | Chiron Corp., Emeryville, CA |
| Alemtuzumab (IgG1κ anti CD52 antibody) | Campath ® | Millennium and ILEX Partners, LP, Cambridge, MA |
| Alitretinoin (9-cis-retinoic acid) | Panretin ® | Ligand Pharmaceuticals, Inc., San Diego CA |
| Allopurinol (1,5-dihydro-4H-pyrazolo[3,4-d]pyrimidin-4-one monosodium salt) | Zyloprim ® | GlaxoSmithKline, Research Triangle Park, NC |
| Altretamine (N,N,N',N',N'',N''-hexamethyl-1,3,5-triazine-2,4,6-triamine) | Hexalen ® | US Bioscience, West Conshohocken, PA |
| Amifostine (ethanethiol, 2-[(3-aminopropyl)amino]-, dihydrogen phosphate (ester)) | Ethyol ® | US Bioscience |
| Anastrozole (1,3-Benzenediacetonitrile, a,a,a',a'-tetramethyl-5-(1H-1,2,4-triazol-1-ylmethyl)) | Arimidex ® | AstraZeneca Pharmaceuticals, LP, Wilmington, DE |
| Arsenic trioxide | Trisenox ® | Cell Therapeutic, Inc., Seattle, WA |
| Asparaginase (L-asparagine amidohydrolase, type EC-2) | Elspar ® | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | Tice BCG ® | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin ® | Ligand Pharmaceuticals |
| bexarotene gel | Targretin ® | Ligand Pharmaceuticals |
| Bleomycin (cytotoxic glycopeptide antibiotics produced by *Streptomyces verticillus*; bleomycin $A_2$ and bleomycin $B_2$) | Blenoxane ® | Bristol-Myers Squibb Co., NY, NY |
| Capecitabine (5'-deoxy-5-fluoro-N-[(pentyloxy)carbonyl]-cytidine) | Xeloda ® | Roche |
| Carboplatin (platinum, diammine [1,1-cyclobutanedicarboxylato(2-)-0,0']-, (SP-4-2)) | Paraplatin ® | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex ® | Searle Pharmaceuticals, England |

TABLE 1-continued

| | | |
|---|---|---|
| Chlorambucil (4-[bis(2chlorethyl)amino]benzenebutanoic acid) | Leukeran ® | GlaxoSmithKline |
| Cisplatin ($PtCl_2H_6N_2$) | Platinol ® | Bristol-Myers Squibb |
| Cladribine (2-chloro-2'-deoxy-b-D-adenosine) | Leustatin ®, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan ®, Neosar ® | Bristol-Myers Squibb |
| Cytarabine (1-b-D-Arabinofuranosylcytosine, $C_9H_{13}N_3O_5$) | Cytosar-U ® | Pharmacia & Upjohn Company |
| cytarabine liposomal | DepoCyt ® | Skye Pharmaceuticals, Inc., San Diego, CA |
| Dacarbazine (5-(3,3-dimethyl-1-triazeno)-imidazole-4-carboxamide (DTIC)) | DTIC-Dome ® | Bayer AG, Leverkusen, Germany |
| Dactinomycin, actinomycin D (actinomycin produced by *Streptomyces parvullus*, $C_{62}H_{86}N_{12}O_{16}$) | Cosmegen ® | Merck |
| Darbepoetin alfa (recombinant peptide) | Aranesp ® | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome ® | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine ® | Wyeth Ayerst, Madison, NJ |
| Denileukin diftitox (recombinant peptide) | Ontak ® | Seragen, Inc., Hopkinton, MA |
| Dexrazoxane ((S)-4,4'-(1-methyl-1,2-ethanediyl)bis-2,6-piperazinedione) | Zinecard ® | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere ® | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin ®, Rubex ® | Pharmacia & Upjohn Company |
| doxorubicin | Adriamycin ® PFS Intravenous injection | Pharmacia & Upjohn Company |
| doxorubicin liposomal | Doxil ® | Sequus Pharmaceuticals, Inc., Menlo park, CA |
| dromostanolone propionate (17b-Hydroxy-2a-methyl-5a-androstan-3-one propionate) | Dromostanolone ® | Eli Lilly & Company, Indianapolis, IN |
| dromostanolone propionate | Masterone ® injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence ® | Pharmacia & Upjohn Company |
| Epoetin alfa (recombinant peptide) | Epogen ® | Amgen, Inc |
| Estramustine (estra-1,3,5(10)-triene-3,17-diol(17beta))-, 3-[bis(2-chloroethyl)carbamate] 17-(dihydrogen phosphate), disodium salt, | Emcyt ® | Pharmacia & Upjohn Company |

TABLE 1-continued

| | | |
|---|---|---|
| monohydrate, or estradiol 3-[bis(2-chloroethyl)carbamate] 17-(dihydrogen phosphate), disodium salt, monohydrate) | | |
| Etoposide phosphate (4'-Demethylepipodophyllotoxin 9-[4,6-O-(R)-ethylidene-(beta)-D-glucopyranoside], 4'-(dihydrogen phosphate)) | Etopophos ® | Bristol-Myers Squibb |
| etoposide, VP-16 (4'-demethylepipodophyllotoxin 9-[4,6-O-(R)-ethylidene-(beta)-D-glucopyranoside]) | Vepesid ® | Bristol-Myers Squibb |
| Exemestane (6-methylenandrosta-1,4-diene-3,17-dione) | Aromasin ® | Pharmacia & Upjohn Company |
| Filgrastim (r-metHuG-CSF) | Neupogen ® | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara ® | Berlex Laboratories, Inc., Cedar Knolls, NJ |
| Fluorouracil, 5-FU (5-fluoro-2,4(1H,3H)-pyrimidinedione) | Adrucil ® | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex ® | IPR Pharmaceuticals, Guayama, Puerto Rico |
| Gemcitabine (2'-deoxy-2',2'-difluorocytidine monohydrochloride (b-isomer)) | Gemzar ® | Eli Lilly |
| Gemtuzumab Ozogamicin (anti-CD33 hP67.6) | Mylotarg ® | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex ® Implant | AstraZeneca Pharmaceuticals |
| Hydroxyurea | Hydrea ® | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin ® | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin ® | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX ® | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec ® | Novartis AG, Basel, Switzerland |
| Interferon alfa-2a (recombinant peptide) | Roferon ®-A | Hoffmann-La Roche, Inc., Nutley, NJ |
| Interferon alfa-2b (recombinant peptide) | Intron A ® (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b]quinoline-3,14(4H,12H) dione hydrochloride trihydrate) | Camptosar ® | Pharmacia & Upjohn Company |
| Letrozole (4,4'-(1H-1,2,4-Triazol-1-ylmethylene) dibenzonitrile) | Femara ® | Novartis |

TABLE 1-continued

| | | |
|---|---|---|
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin ®, Leucovorin ® | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol ® | Janssen Research Foundation, Titusville, NJ |
| Lomustine (1-(2-chloro-ethyl)-3-cyclohexyl-1-nitrosourea) | CeeNU ® | Bristol-Myers Squibb |
| Meclorethamine, nitrogen mustard (2-chloro-N-(2-chloroethyl)-N-methylethanamine hydrochloride) | Mustargen ® | Merck |
| Megestrol acetate 17α(acetyloxy)-6-methylpregna-4,6-diene-3,20-dione | Megace ® | Bristol-Myers Squibb |
| Melphalan, L-PAM (4-[bis(2-chloroethyl) amino]-L-phenylalanine) | Alkeran ® | GlaxoSmithKline |
| Mercaptopurine, 6-MP (1,7-dihydro-6H-purine-6-thione monohydrate) | Purinethol ® | GlaxoSmithKline |
| Mesna (sodium 2-mercaptoethane sulfonate) | Mesnex ® | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex ® | Therakos, Inc., Way Exton, Pa |
| Mitomycin C | Mutamycin ® | Bristol-Myers Squibb |
| mitomycin C | Mitozytrex ® | SuperGen, Inc., Dublin, CA |
| Mitotane (1,1-dichloro-2-(o-chlorophenyl)-2-(p-chlorophenyl) ethane) | Lysodren ® | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone ® | Immunex Corporation |
| Nandrolone phenpropionate | Durabolin ®-50 | Organon, Inc., West Orange, NJ |
| Nofetumomab | Verluma ® | Boehringer Ingelheim Pharma KG, Germany |
| Oprelvekin (IL-11) | Neumega ® | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin ® | Sanofi Synthelabo, Inc., NY, NY |
| Paclitaxel (5β, 20-Epoxy-1,2a,4,7β,10β,13a-hexahydroxytax-11-en-9-one 4,10-diacetate 2-benzoate 13-ester with (2R,3S)-N-benzoyl-3-phenylisoserine) | Taxol ® | Bristol-Myers Squibb |
| Pamidronate (phosphonic acid (3-amino-1-hydroxypropylidene) bis-, disodium salt, pentahydrate, (APD)) | Aredia ® | Novartis |
| Pegademase ((monomethoxypolyethylene glycol succinimidyl) 11-17-adenosine deaminase) | Adagen ® (Pegademase Bovine) | Enzon Pharmaceuticals, Inc., Bridgewater, NJ |
| Pegaspargase (monomethoxypolyethylene glycol succinimidyl L-asparaginase) | Oncaspar ® | Enzon |
| Pegfilgrastim (covalent conjugate of recombinant methionyl human G-CSF (Filgrastim) and monomethoxypolyethylene glycol) | Neulasta ® | Amgen, Inc |
| Pentostatin | Nipent ® | Parke-Davis Pharmaceutical Co., Rockville, MD |
| Pipobroman | Vercyte ® | Abbott Laboratories, Abbott Park, IL |
| Plicamycin, Mithramycin (antibiotic produced by *Streptomyces plicatus*) | Mithracin ® | Pfizer, Inc., NY, NY |

TABLE 1-continued

| | | |
|---|---|---|
| Porfimer sodium | Photofrin ® | QLT Phototherapeutics, Inc., Vancouver, Canada |
| Procarbazine (N-isopropyl-μ-(2-methylhydrazino)-p-toluamide monohydrochloride) | Matulane ® | Sigma Tau Pharmaceuticals, Inc., Gaithersburg, MD |
| Quinacrine (6-chloro-9-(1-methyl-4-diethyl-amine) butylamino-2-methoxyacridine) | Atabrine ® | Abbott Labs |
| Rasburicase (recombinant peptide) | Elitek ® | Sanofi-Synthelabo, Inc., |
| Rituximab (recombinant anti-CD20 antibody) | Rituxan ® | Genentech, Inc., South San Francisco, CA |
| Sargramostim (recombinant peptide) | Prokine ® | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar ® | Pharmacia & Upjohn Company |
| Talc ($Mg_3Si_4O_{10}(OH)_2$) | Sclerosol ® | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex ® | AstraZeneca Pharmaceuticals |
| Temozolomide (3,4-dihydro-3-methyl-4-oxoimidazo[5,1-d]-as-tetrazine-8-carboxamide) | Temodar ® | Schering |
| teniposide, VM-26 (4'-demethylepipodophyllotoxin 9-[4,6-0-(R)-2-thenylidene-(beta)-D-glucopyranoside]) | Vumon ® | Bristol-Myers Squibb |
| Testolactone (13-hydroxy-3-oxo-13,17-secoandrosta-1,4-dien-17-oic acid [dgr]-lactone) | Teslac ® | Bristol-Myers Squibb |
| Thioguanine, 6-TG (2-amino-1,7-dihydro-6H-purine-6-thione) | Thioguanine ® | GlaxoSmithKline |
| Thiotepa (Aziridine, 1,1',1''-phosphinothioylidynetris-, or Tris (1-aziridinyl) phosphine sulfide) | Thioplex ® | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin ® | GlaxoSmithKline |
| Toremifene (2-(p-[(Z)-4-chloro-1,2-diphenyl-1-butenyl]-phenoxy)-N,N-dimethylethylamine citrate (1:1)) | Fareston ® | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar ® | Corixa Corp., Seattle, WA |
| Trastuzumab (recombinant monoclonal $IgG_1$ kappa anti-HER2 antibody) | Herceptin ® | Genentech, Inc |
| Tretinoin, ATRA (all-trans retinoic acid) | Vesanoid ® | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar ® | Anthra --> Medeva |
| Vinblastine, Leurocristine ($C_{46}H_{56}N_4O_{10} \bullet H_2SO_4$) | Velban ® | Eli Lilly |
| Vincristine ($C_{46}H_{56}N_4O_{10} \bullet H_2SO_4$) | Oncovin ® | Eli Lilly |
| Vinorelbine (3',4'-didehydro-4'-deoxy-C'- | Navelbine ® | GlaxoSmithKline |

TABLE 1-continued

| | | |
|---|---|---|
| norvincaleukoblastine [R-(R*,R*)-2,3-dihydroxybutanedioate (1:2)(salt)]) | | |
| Zoledronate, Zoledronic acid ((1-Hydroxy-2-imidazol-1-yl-phosphonoethyl) phosphonic acid monohydrate) | Zometa ® | Novartis |

Numerous other examples of chemotherapeutic compounds and anticancer therapies suitable for co-administration with the disclosed compositions are known to those skilled in the art.

In some embodiments, the compositions of the present invention are especially useful when co-administered with an anti-cancer drug whose cytotoxicity is due primarily to the production of reactive oxygen species, for example, doxorubicin, daunorubicin, mitocyn C, etoposide, cisplatin, arsenic tioxide, ionizing radiation and photodynamic therapy.

Anticancer agents further include compounds which have been identified to have anticancer activity but are not currently approved by the United States Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference, Goodman and Gilman's "Pharmaceutical Basis of Therapeutics" 10th Edition, Eds. Hardman et al., 2002 and later editions, and "Biologic Therapy of Cancer, 2nd Edition, Eds. DeVita et al., 1995, JB Lippincott Co. Publ, p. 919 and later editions, incorporated herein by reference in their entireties.

In some embodiments, GSH levels in cells, for example both normal and tumor cells, are reduced prior to the administration of compounds of Formula I, II, or III. By lowering GSH levels in all cells, cancer cells become vulnerable to therapies. However, following treatment with Formula I, II, or III, normal cells are made substantially more resistant to the toxic effects of the cancer therapies. Thus, in these embodiments, cancer cells are supersensitized to therapy, while normal cells are protected. The present invention is not limited by the nature of the compound or treatment used to reduce GSH levels.

In one embodiment, the present invention provides for the use and administration of 2-amino-4-(S-butylsulfonimidoyl) butanoic acid (buthionine sulfoximine or BSO) in conjunction with the compositions of the present invention. In some embodiments, buthionine sulfoximine inhibits the synthesis of GSH in both non-tumor and tumor cells by inhibiting γ-glutamulcysteine synthetase, an essential enzyme for synthesis of GSH, and a composition of the present invention replenishes GSH in non-tumor cells. In some embodiments, BSO is administered prior to the administration of a composition of the present invention. In some embodiments, BSO is administered in conjunction with a compositions of the present invention. In some embodiments, the BSO and a composition of the present invention are administered prior to, at the same time, or after the administration of chemotherapeutics and/or radiotherapy to a subject. It is contemplated that as BSO decreases the amount of GSH in tumor and non-tumor cells, the addition of a composition of the present invention replenishes GSH in non-tumor cells but not tumor cells, as such the tumor cells maintain low or non-existent GSH levels throughout the administration of chemotherapeutic drugs and/or radiotherapy. The low or non-existent levels of GSH in tumor cells following administration of BSO strips them of the protective effects that GSH offers tumor cells, thereby allowing for more efficient targeting and eradication of the tumor cells by chemo and radiation therapies. In some embodiments, the administration of BSO and a compound of the present invention allows for the administration of lesser amounts (potentially for longer time periods) of chemotherapeutic drugs than normal due to the low or non-existent levels of GSH in tumor cells, and at the same time the non-tumor cells of a subject are less exposed to the toxic effects of the therapy.

In some embodiments, the compositions of the present invention are useful in preparation as adjuvants to chemo and/or anticancer therapy and radiation therapy. The methods and techniques for preparing medicaments comprising a composition of the present invention are well-known in the art. Exemplary pharmaceutical formulations and routes of delivery are described below. One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

In some embodiments of the present invention, the compositions are administered alone, while in some other embodiments, the compositions are preferably present in a pharmaceutical formulation comprising at least one active ingredient/agent, as defined above, together with one or more pharmaceutically acceptable carriers and optionally other therapeutic agents. Each carrier should be "acceptable" in the sense that it is compatible with the other ingredients of the formulation and not injurious to the subject.

Formulations include, for example, parenteral administration (e.g., subcutaneous, intramuscular, intravenous, intradermal) and site-specific administration. In some embodiments, formulations are conveniently presented in unit dosage form and are prepared by any method known in the art of pharmacy. Such methods include the step of bringing into association the active ingredient with the carrier that constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

Various delivery systems are known and can be used to administer compositions of the present invention. Methods of delivery include, but are not limited to, intra-arterial, intramuscular, intravenous, and site specific. For example, in some embodiments, it may be desirable to administer the compositions of the invention locally to the area targeted by chemo and/or anticancer therapies and/or radiation therapy; this may be achieved by, for example, and not by way of limitation, local infusion during surgery, injection, or by means of a catheter.

In some embodiments, in vivo administration of the compositions as described herein is effected in one dose, continuously or intermittently throughout the course of treatment. Methods of determining the most effective means and dosage of administration are well known to those of skill in the art and vary with, for example, the composition used for therapy, the target cell being treated and the subject being treated. Single or multiple administrations are carried out with the dose level and pattern being selected by the treating physician. In some embodiments, the compositions as described herein are delivered to the subject prior to administration of the chemotherapeutic agent. In some embodiments, compositions as described herein are delivered on a daily basis (e.g., at least once, at least twice, at least three times) and accompany the administration of radiotherapy.

Suitable dosage formulations and methods of administering the agents are readily determined by those of skill in the art. When the compositions described herein are co-administered with another chemoprotective agent, the effective amount may be less than when the agent is used alone. Ideally, the agent should be administered to achieve peak concentrations of the active compound at the target sites for chemo and radiation therapy. Desirable blood levels of the agent may be maintained by a continuous infusion to provide a therapeutic amount of the active ingredient within the target tissue.

The present invention also includes methods involving co-administration of the compositions described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when treating cancer, the additional agent is a chemotherapeutic agent, anti-cancer agent, or radiation. The additional agents to be co-administered, such as anticance can be any of the well-known agents in the art, including, but not limited to, those that are currently in clinical use (see Table I for exemplary agents). The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The compositions and methods described herein address both these problems. Drug resistance, where increasing dosages are required to achieve therapeutic benefit, is overcome by co-administering the compositions described herein with the known agent. The compositions described herein protect cells and tissues from toxic effects of chemotherapeutic drugs and radiation therapy and, accordingly, less of these agents are needed to achieve a therapeutic benefit. Conversely, the protection of normal cells and tissues against the toxic effects of anticancer therapies by co-administration of the compositions as described herein allows for higher doses and/or longer treatment regimens when using such therapies, thereby providing the medical practitioner with the tools to follow a more aggressive anticancer strategy than was otherwise deemed possible.

In some embodiments, the present invention provides methods for using the compositions as described herein for screening for the efficacy of such compositions in inhibiting or decreasing toxicity in cells and tissues when such cells and tissues are administered cancer, or other, therapies that are toxic to normal cells. In some embodiments, methods for screening are conducted in vitro. In other embodiments, these screens are conducted in vivo. In some embodiments, methods of the present invention are performed in vivo in non-human animals or human subjects. In some embodiments, the methods screen for the inhibition or decrease of apoptosis is cells, in vitro or in vivo, when such cells, non-human animals, or human subjects are co-administered a cancer, or other, therapy in combination with compositions of the present invention. In some embodiments, such methods define efficacy of the compositions as described herein for use in decreasing or inhibiting the toxic effects of therapies by comparing results from a screen with a composition of the present invention to a screen performed without said composition (e.g., control experiment). Toxic effects of therapies on cells includes cellular death by apoptosis as a result of the therapy. A composition of the present invention that is efficacious in inhibiting or decreasing the toxic effects of therapies is one that inhibits or decreases cellular apoptosis in normal, non-diseased cells when toxic therapies are administered. A skilled artisan will understand methods for determining cellular apoptosis. These methods include, but are not limited to, measuring apoptotic indicator enzymes such as caspase 3/7, 8 or 9, TdT-mediated dUTP Nick-End Labeling (TUNEL) assays, and apoptosis related antibodies (e.g., anti-PARD, anti-caspase 3, etc.). Detection methods utilized with apoptotic assays include fluorometric, luminescent, and colorimetric.

In some embodiments, such in vivo uses are, for example, performed by taking a subject (e.g., human or non-human animal) with cancer and co-administering a therapy regimen in conjunction with a composition of the present invention, and comparing the outcome of such an administration with a subject that received the same therapy regimen without co-administration of a composition of the present invention.

In some embodiments, such in vitro uses are, for example, performed in tissue culture dishes with primary or immortalized tissue culture cells (e.g., HeLa, HEK293, CHO, 3T3, etc.) or tissue explants. In such in vitro uses, a composition of the present invention is co-administered with a therapy regimen known to be toxic to normal cells, the results being compared with results from tissue culture cells or explants that receive the same therapy regimen without a composition of the present invention.

Experimental

The following examples are provided in order to demonstrate and further illustrate certain preferred embodiments and aspects of the present invention and are not to be construed as limiting the scope thereof. In the experimental disclosure which follows, the following abbreviations apply: equiv (equivalents); M (Molar); N (Normal); mol (moles); mmol (millimoles); g (grams); L (liters); ml (milliliters); ° C. (degrees Centigrade); min. (minutes); % (percent); psi (pounds per square inch).

EXAMPLE 1

Preparation of PBS1000

Synthesis of
2-benzyloxycarbonylamino-4-carbamoyl-butyric
acid (1)

Glutamine (36.5 g, 0.25 mol) was stirred with 1M sodium bicarbonate (750 ml) and toluene (200 ml). Benzyl chloroformate (50 ml, 59.75 g, 0.35 mol, 1.4 equiv.) was added drop-wise over 20 min. and the resulting mixture was stirred under nitrogen at room temperature overnight. Ethyl acetate (400 ml) was added and phases were separated. The organic phase was extracted with water (50 ml) and discarded. The aqueous phase was acidified with 6N hydrochloric acid and extracted with ethyl acetate (2×600 ml). The combined extracts were washed with water (100 ml) and stripped. The residue was dried in a vacuum oven (50° C.) to produce (1) (64 g, 91.4%).

Synthesis of
2-benzyloxycarbonylamino-4-carbamoyl-butyric
acid ethyl ester (2)

A mixture of acid (1) (64 g, 0.228 mol), dimeththylformamide (210 ml) and sodium bicarbonate (111 g, 1.32 mol, 5.8 equiv.) was stirred at room temperature for 30 min. Ethyl iodide (34 ml, 66.3 g, 0.425 mol, 1.86 equiv.) was added and stirring was continued overnight under nitrogen. The reaction mixture was slowly diluted with water to 1 L and stirred for 40 min. The solid was collected by filtration, washed well with water and partitioned between ethyl acetate (8 L) and water (3 L). Phases were separated and the aqueous phase was extracted with ethyl acetate (2.5 L). The combined organic extracts were washed with water (1 L), dried over sodium sulfate, stripped and dried in a vacuum oven (50° C.) to produce (2) (47 g, 66.7%).

Synthesis of
2-benzyloxycarbonylamino-pentanedioic acid
1-ethyl ester (3)

A suspension of the amide (2) (38 g, 0.1233 mol) in anhydrous acetonitrile (400 ml) was stirred at reflux under nitrogen and t-butyl nitrite (35 ml, 3.17 equiv.) was added quickly. The reflux was continued for 2 hrs. After cooling, the solvent was removed in a rotary evaporator. The residue was taken in water (250 ml) and ethyl acetate (500 ml) and the biphasic mixture was stirred well while solid sodium bicarbonate was slowly added to pH=7.5. Phases were separated and the organic phase was washed with 10% sodium bicarbonate (200 ml). The combined aqueous extracts were washed with ethyl acetate (300 ml), made acidic with 6N hydrochloric acid and extracted with ethyl acetate (2×300 ml). The combined extracts were washed with water (150 ml), dried over sodium sulfate, stripped and the residue was dried in a vacuum oven (50° C.) to produce (3) (24.6 g, 64.7%).

Synthesis of 2-benzyloxycarbonylamino-4-(1-
ethoxycarbonyl-2-hydroxy-ethylcarbamoyl)-butyric
acid ethyl ester (4)

A suspension of acid (3) (7.6 g, 24.57 mmol) in dry acetonitrile (80 ml) was stirred under nitrogen at room temperature and Hobt (4 g, 29.6 mmol, 1.2 equiv.) was added. Stirring was continued for 10 min., and EDCI (5.1 g, 26.6 mmol, 1.1 equiv.) was added. The resulting mixture was stirred for 1.5 hrs and serine ethyl ester free base (3.27 g, 24.57 mmol, 1 equiv.) in acetonitrile (20 ml) was added. Stirring was continued at room temperature for 3 hrs. The solvent was removed in a rotary evaporator, the residue was partitioned between water (100 ml) and ethyl acetate (200 ml) and phases were separated. The organic phase was washed successively with water (50 ml), 5% potassium carbonate (2×50 ml) and water (2×50 ml), dried over sodium sulfate and the solvent removed in a rotary evaporator. The residue was dried in a vacuum oven (50° C.) to produce (4) (12.4 g, 85.5%).

Synthesis of 2-amino-4-(1-ethoxycarbonyl-2-hydroxy-ethylcarbamoyl)-butyric acid ethyl ester (5)

A solution of (4) (11.4 g, 26.86 mmol) in ethanol (225 ml) containing 1.2 g 20% palladium on activated carbon (50% wet) was hydrogenated at 30 psi for 3 hrs. The catalyst was removed by filtration and the solution was washed with ethanol. The solvent was removed in a rotary evaporator. The residue was dried in a vacuum oven (50° C.) to produce (5) (5.86 g, 75%).

Synthesis of 3-(2-chloro-1-ethoxycarbonyl-ethylcarbamoyl)-1-ethoxycarbonyl-propyl-ammonium chloride (6)

A solution of alcohol (5) (0.29 g, 1 mmol) in dichloromethane (10 ml) was treated with thionyl chloride (1 g) and stirred at room temperature under nitrogen overnight. The solvent was removed on a rotary evaporator (bath temperature below 28° C.). Dichloromethane (10 ml) was added and stripped under the same conditions twice. The solid residue was taken in water (8 ml) and washed with MTBE (2×15 ml). The resulting aqueous solution contains pure (6) (LCMS) and was used as such in the next step.

Synthesis of (S)-ethyl 2-amino-5-((R)-1-ethoxy-1-oxo-3-(phosphonothio)propan-2-ylamino)-5-oxopentanoate monosodium salt(7)

A solution of trisodium thiophosphate (0.4 g) in water (6 ml) was stirred at room temperature under nitrogen and the solution of (6) prepared above was added all at once. The reaction mixture was stirred at room temperature under nitrogen overnight. The pH was carefully adjusted to 8.0 with acetic acid and the resulting solution was run through a reverse phase column (P18) using water as the eluent. Fractions were checked by LCMS and those containing the product were evaporated to dryness (oil pump vacuum, bath temperature below 25° C.) to produce 47 mg of (7). LCMS (M=386), $^1$H NMR and $^{31}$P NMR were used to confirm the final structure (7).

Example 2

Dephosphorylation of (S)-ethyl 2-amino-5-((R)-1-ethoxy-1-oxo-3-(phosphonothio)propan-2-ylamino)-5-oxopentanoate monosodium salt Assays were performed to verify the ability of alkaline phosphatase to dephosphorylate compound (7) to create sulfydryl reactive groups. Calf intestinal alkaline phosphatase (CIAP, Sigma) was diluted in phosphate buffered saline (PBS) to 250 units/ml, and frozen in tubes containing 100 μl aliquots. The following solutions were prepared; 2 mM glutathione (GSH), 1.05 mM DTNB (5-5'-Dithio-bis-(2-nitrobenzoic acid; also known as Ellman's Reagent) and 5 mM amifostine (AF; 1 mg/ml). Alkaline phosphatase activity, and the ability of the assay to measure reactive sulfhydryl groups in solution, were evaluated initially using amifostine as the control composition. Absorbances were measured at $A_{412}$. An increase in absorbance is indicative of free reactive sulfhydryl groups present in the reaction. Reaction conditions and results are found in Table 2; volumes are in μls, reaction 1 was incubated for 5 min. at room temperature prior to absorbance reading, and reactions 2-5 were incubated for 10 min. at room temperature prior to absorbance readings.

TABLE 2

| REACTION | GSH | AF | CIAP | DTNB | PBS | A412 |
|---|---|---|---|---|---|---|
| 1 | 10 | | | 100 | 890 | 0.35 |
| 2 | | 10 | | | 890 | 0.00 |
| 3 | | 10 | 25 | | 865 | 0.00 |
| 4 | | 20 | 50 | 100 | 880 | 0.03 |
| 5 | | 20 | 50 | 100 | 830 | 0.34 |

As seen in Table 2, the positive control (reaction 1) and the test reaction 5 (with amifostine) have similar absorbance readings, indicating that the reaction conditions are capable of measuring free sulfhydryl groups after dephosphorylation of a compound with alkaline phosphatase (reaction 5).

A second assay was performed to examine the ability of alkaline phosphatase to dephosphorylate compound (7) to create sulfydryl reactive groups. A 12.5 mM solution of Compound 7 was made (4 mg/ml) and used in the test reactions. Reaction conditions and results are found in Table 3; volumes are in μls, reactions were incubated for 10 min. at 37° C. prior to absorbance readings, duplicates of the Compound 7 (C7) negative reaction (without CIAP; reactions 6 & 8) and Compound 7 test reaction (with CIAP; reactions 7 & 9) were performed.

TABLE 3

| REACTION | C7 | CIAP | DTNB | PBS | A412 |
|---|---|---|---|---|---|
| 6 | 10 | | 100 | 890 | 0.044 |
| 7 | 10 | 50 | 100 | 840 | 0.547 |
| 8 | 10 | | 100 | 890 | 0.039 |
| 9 | 10 | 50 | 100 | 840 | 0.526 |
| 10 | | 50 | 100 | 850 | 0.015 |

As seen in Table 3, Compound 7 is dephosphorylated by alkaline phosphatase to yield free reactive sulfhydryl groups. Such reactive sulfhydryl groups are capable of capturing free oxygen radicals created by chemotherapy and/or radiation therapy, thereby inhibiting or decreasing toxicity of these compounds to normal cells and tissues. A time course of dephosphorylation was also performed using Compound 7, following the same reaction conditions as in Table 3. The time course showed that over a 30 min. period ($A_{412}$ readings taken at 3 min. intervals) the dephosphorylation of Compound 7 was time dependent, as an increase in free sulfhydryl groups was seen over time.

Example 3

Intracellular Activity

The compound ((S)-ethyl 2-amino-5-((R)-1-ethoxy-1-oxo-3-(phosphonothio)propan-2-ylamino)-5-oxopentanoate monosodium salt) was tested for intracellular properties. In particular, experiments were conducted to determine the ability of the compound to enter into cells and generate glutathione. HepG2 were incubated with the compound with or without added bovine intestinal alkaline phosphatase (Sigma). Cells were scraped into SSA, vortexed and then spun. GSH in the supernatants were analyzed utilizing the glutathione reductase method of Tietze (Tietze F: "ENZYMIC METHOD FOR QUANTITATIVE DETERMINATION OF NANOGRAM AMOUNTS OF TOTAL AND OXIDIZED GLUTATHIONE APPLICATIONS TO MAM- MALIAN BLOOD AND OTHER TISSUES" Analytical Biochemistry, 27(3): 502-522 (1969)). The compound did not enter cells unless the phosphate group was first hydrolyzed with alkaline phosphatase. Cells treated with the compound and alkaline phosphatase had a 3.6 fold increase in their GSH contents. Importantly, this increase in cellular GSH levels also occurred in the presence of buthionine sulfoximine (greater than 5 fold increase in cellular GSH), indicating that the compound was not simply delivering cysteine or other building blocks for GSH synthesis but rather delivering gamma-glutamyl cysteine. Cells incubated with compound with or without alkaline phosphatase did not exhibit any evidence of toxicity.

In experiments with mice and hamsters, no overt toxicity was observed, with testing conducted at doses up to 5 mmoles/animal.

Example 4

Scale-Up Synthesis

The following example provides a protocol for generating gram quantities of (S)-ethyl 2-amino-5-((R)-1-ethoxy-1-oxo-3-(phosphonothio)propan-2-ylamino)-5-oxopentanoate monosodium salt.

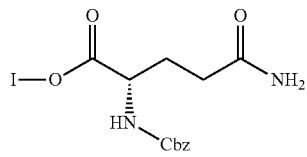 [SMILES: NC(=O)CC[C@H](NC(=O)OCc1ccccc1)C(=O)OI]

L-Glutamine (500 g, 3.42 mol) was stirred with 1M sodium bicarbonate (10.26 L) and toluene (2.75 L). Benzyl chloroformate (684 ml, 818 g, 4.8 mol, 1.4 equiv.) was added dropwise over 60 min. and the resulting mixture was stirred under nitrogen at room temperature overnight. Ethyl acetate (6 L) was added, phases were separated. The organic phase was extracted with water (1 L) and discarded. The aqueous phase was made acidic with 6N hydrochloric acid (~1.6 L) and extracted with ethyl acetate (3×6 L). The combined extracts were washed with water (2 L), brine (2 L) and dried over sodium sulfate. After filtration, the filtrate was concentrated in vacuo to give a residue which was triturated with MTBE. The solid was filtered and was dried in a vacuum oven (45° C.) to yield (823.4 g, 86%) of a solid.

MS (ESP): 303.0 (M+Na$^+$) for $C_{13}H_{16}N_2O_5$

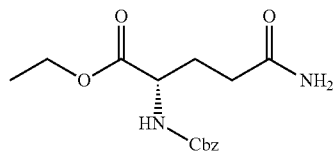 [SMILES: CCOC(=O)[C@H](CCC(N)=O)NC(=O)OCc1ccccc1]

A mixture (S)-5-amino-2-(benzyloxycarbonylamino)-5-oxopentanoic acid of (823 g, 2.94 mol), dimethylformamide (3 L) and sodium bicarbonate (1.481 Kg, 17.6 mol, 6 equiv.) was stirred at room temperature for 60 min. Ethyl iodide (447 ml, 871 g, 5.6 mol, 1.9 equiv.) was added dropwise over 60 min. and stirring was continued for 4 days under nitrogen. The reaction mixture was slowly diluted with water (10 L) and stirred for 60 min. The solid was collected by filtration, washed with water (8 L) and dried in a convection oven (50° C.) for 4 days to yield (905 g, 100%) of a solid.

MS (ESP): 331.2 (M+Na$^+$) for $C_{15}H_{20}N_2O_5$

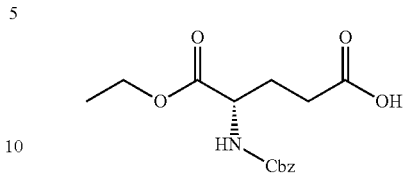

A suspension of the (S)-ethyl 5-amino-2-(benzyloxycarbonylamino)-5-oxopentanoate (570 g, 1.85 mol) in anhydrous acetonitrile (6 L) was stirred at reflux under nitrogen and t-butyl nitrite (650 mL, 3.0 equiv.) was added quickly. The reflux was continued for 2 hrs. After cooling, the solvent was removed in a rotary evaporator. The residue was taken in water (1.5 L) and ethyl acetate (3 L) and the biphasic mixture was stirred well while solid sodium bicarbonate was slowly added to pH=7.5. Phases were separated and the organic phase was washed with 10% sodium bicarbonate (6×500 ml). The combined aqueous extracts were washed with ethyl acetate (1 L), made acidic with 6N hydrochloric acid and extracted with ethyl acetate (4×750 ml). The combined extracts were dried over sodium sulfate and concentrated in vacuo to yield (398 g, 70%) of a solid.

MS (ESP): 332.0 (M+Na$^+$) for $C_{15}H_{19}NO_6$

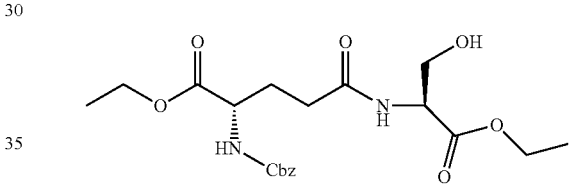

A suspension of (S)-4-(benzyloxycarbonylamino)-5-ethoxy-5-oxopentanoic acid (398 g, 1.29 mol) in dry acetonitrile (4 L) was stirred under nitrogen at room temperature and HOBt (209 g, 1.54 mol, 1.2 equiv.) was added. Stirring was continued for 10 min, then EDCI (220 g, 1.42 mol, 1.1 equiv.) was added. The resulting mixture was stirred for 1.5 hrs when serine ethyl ester free base (171 g, 1.29 mol, 1 equiv.) in acetonitrile (1 L) was added. Stirring was continued at room temperature for 16 hrs. The solvent was removed in vacuo and the residue was partitioned between water (4 L) and ethyl acetate (8 L) and phases were separated. The organic phase was washed successively with 5% potassium carbonate (2×2 L) and brine (2×2 L), dried over sodium sulfate and the solvent was removed in vacuo. The residue was triturated with MTBE, filtered and dried in a vacuum oven (45° C.) to yield (381.4 g, 70%) as a solid.

MS (ESP): 447.0 (M+Na$^+$) for $C_{20}H_{28}N_2O_8$

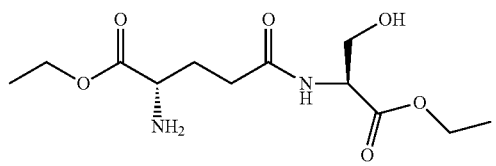 [SMILES: CCOC(=O)[C@H](CO)NC(=O)CC[C@H](N)C(=O)OCC]

A solution of (S)-ethyl 2-(benzyloxycarbonylamino)-5-((S)-1-ethoxy-3-hydroxy-1-oxopropan-2-ylamino)-5-oxopentanoate (381 g, 0.90 mol) in ethanol (7.5 L) containing 76 g of 10% palladium on activated carbon (50% water wet) was hydrogenated at 30 psi for 3 hrs. The catalyst was removed by filtration washing the cake with ethanol (4×2 L). The solvent was removed in vacuo and the residue was triturated with MTBE (2 L), filtered and dried in a vacuum oven (45° C.) to yield (235.3 g, 91%) of a tan solid.

MS (ESP): 313.2 (M+Na$^+$) for $C_{12}H_{22}N_2O_6$

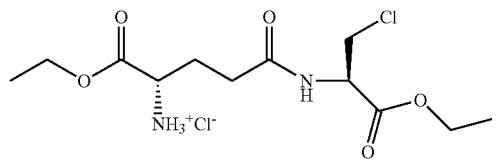

A solution of (S)-ethyl 2-amino-5-((S)-1-ethoxy-3-hydroxy-1-oxopropan-2-ylamino)-5-oxopentanoate (10 g, 35 mmol) in dichloromethane (350 ml) was treated with thionyl chloride (20 mL) and stirred at room temperature under nitrogen overnight. The solvent was removed on a rotary evaporator (bath temperature below 28° C.). Dichloromethane (100 ml) was added and stripped under the same conditions twice. The solid residue was triturated with DCM (100 mL), Heptane (100 mL), and MTBE (100 ml), filtered and dried in a vacuum oven (25° C.) to yield (10 g, 84%) of an off-white solid.

MS (ESP): 309.0 (M+H$^+$) for $C_{12}H_{21}ClN_2O_5$

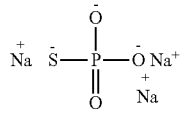

To solution of 40 g of sodium hydroxide in 300 mL of water was added thiophosphoryl chloride (28.6 g, 0.17 mol) in one portion and the resulting biphasic solution is quickly heated to reflux. The reaction mixture is heated at reflux until the thiophosphoryl chloride layer is no longer observed (approx. 30 min.). The heating mantle was removed and the reaction mixture cooled to room temperature. An ice water bath is used to precipitate out the product and sodium salts (approx. 30 minutes at 0° C.). The mixture of product and sodium chloride are filtered off, the solids are collected and dissolved in 150 mL of 45° C. water (removes sodium chloride). Anhydrous methanol (200 mL) is added to precipitate the product which is filtered, collected and stirred under 200 mL of anhydrous methanol for 16 hours to effectively dehydrate the salt. The solids are again collected by filtration and dried in a vacuum oven with no heat for 32 hours to yield (17.3 g, 56.5%) of a white solid.

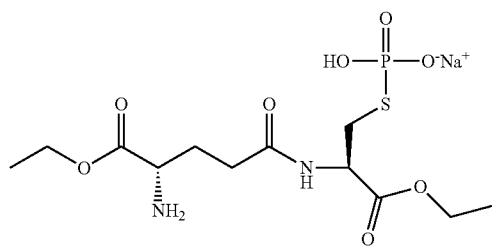

To a 500 mL round bottom flask was added 250 mL DIUF water. Water was then degassed with nitrogen over 20 min. (S)-5-((R)-3-chloro-1-ethoxy-1-oxopropan-2-ylamino)-1-ethoxy-1,5-dioxopentan-2-aminium chloride (5 g, 14.5 mmol) and freshly prepared trisodiumthiophosphate (2.9 g, 16.0 mmol) were added at once. The reaction mixture was stirred at room temperature under nitrogen for 3 days. The aqueous mixture was concentrated to a minimal volume in vacuo keeping the bath temperature below 25° C. The aqueous residue (50 ml/run) was loaded onto an Analogix 300 g flash C18 column using water as the eluent to yield (6.0 g) of a light yellow foamy solid that is very hygroscopic.

MS (ESP): 387.2 (M+H$^+$) for $C_{12}H_{23}N_2O_8PS$ $^1$H NMR: 1.16 (overlapping triplets, 6H), 2.00-2.21 (m, 3H), 2.31-2.43 (m, 2H), 3.01-3.05 (m, 2H), 3.63-4.20 (m, 7 H), 4.41-4.43 (m, 1H); $^{31}$P NMR: 17.35 (d)

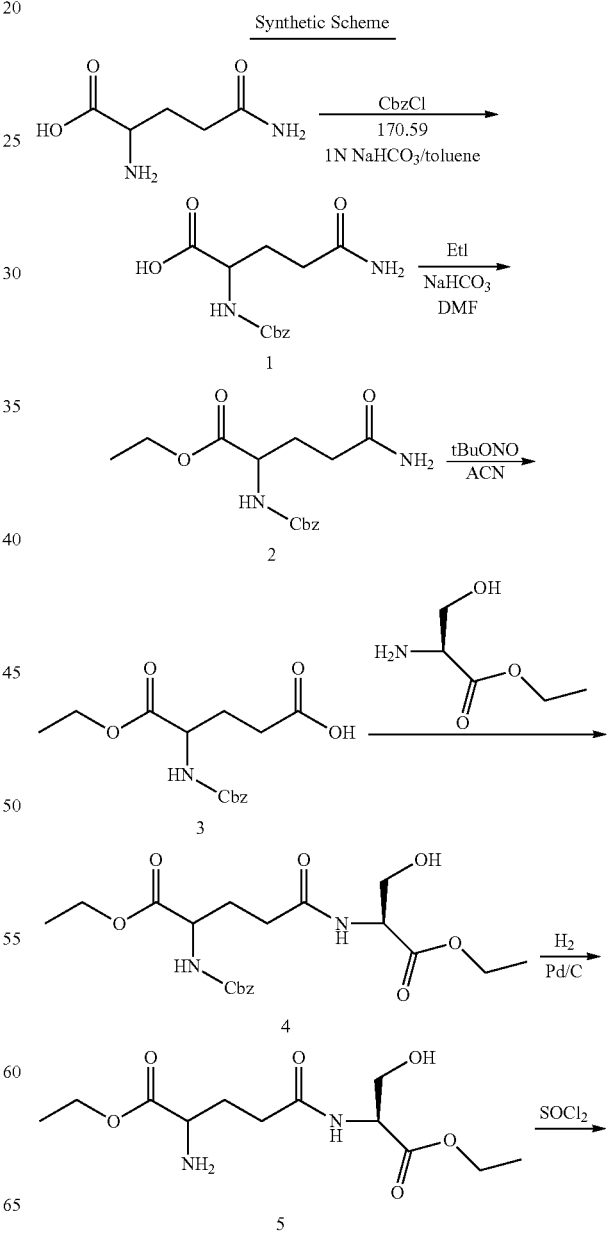

-continued

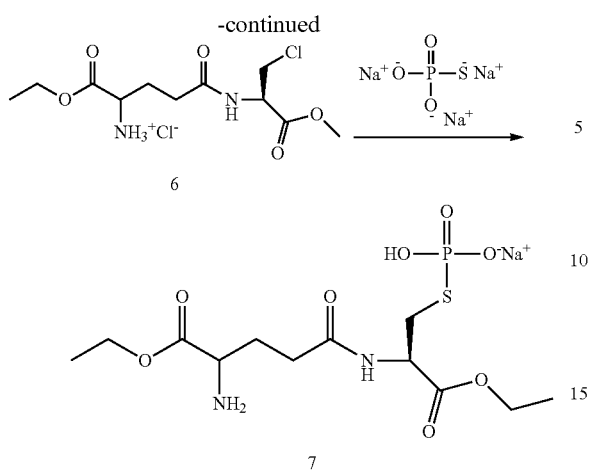

In some embodiments, the following steps are used for producing compound 7 from compound 5.

Synthesis of 3-(2-chloro-1-ethoxycarbonyl-ethylcarbamoyl)-1-ethoxycarbonyl-propyl-ammonium chloride (6)

A solution of alcohol 5 (10 g, 35 mmol) in dichloromethane (350 ml) was treated with thionyl chloride (20 mL) and stirred at room temperature under nitrogen overnight. The solvent was removed on a rotary evaporator (bath temperature below 28° C.). Dichloromethane (100 ml) was added and stripped under the same conditions twice. The solid residue was triturated with DCM (100 mL), Heptane (100 mL), and MTBE (100 ml) to give 10 g (84% yield) of pure 6 (LCMS) as a off-white solid.

Synthesis of Trisodiumthiophosphate: To a flask was charged 40 g (1.0 mol) of sodium hydroxide in 300 mL of water. The solution is stirred until all of the base is dissolved. Thiophosphoryl chloride (28.6 g, 0.17 mol) is added in one portion and the resulting bi-phasic solution is quickly heated to reflux. The reaction mixture is heated at reflux until the thiophosphoryl chloride layer is no longer observed (approx. 30 min). The heating mantle is removed and the reaction mixture cooled to room temperature. An ice water bath is used to precipitate out the product and sodium salts (approx. 30 minutes at 0° C.). The mixture of product and sodium chloride is filtered off, the solids are collected and dissolved in 150 mL of 45'C water (removes sodium chloride) Anhydrous methanol (200 mL) is added to precipitate out the trisodiumphosphoryl chloride. The product is filtered, collected and stirred under 200 mL of anhydrous methanol for 16 hours to effectively dehydrate the salt. The solids are again collected by filtration and dried in a vacuum oven with no heat for 32 hours. 17.3 g of product is obtained in 56.5% yield.

Synthesis of (S)-ethyl 2-amino-5-((R)-1-ethoxy-1-oxo-3-(phosphonothio)propan-2-ylamino)-5-oxopentanoate monosodium salt (7):

To a 500 mL round bottom flask was added 250 mL DIUF water. Water was then degassed by nitrogen over 20 min. 5 g 6 and 2.9 g fresh made trisodiumthiophosphate were added at once. The reaction mixture was stirred at room temperature under nitrogen for 3 days. LC/MS indicated that the major peak is product. Analogix 300 g flash C18 column was then applied to purify the final product to give 6.0 g light yellow clear film.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A composition comprising the compound of the formula:

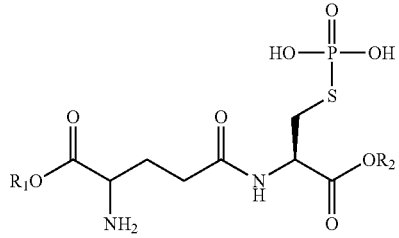

or salts thereof,
wherein:
$R_1$ and $R_2$ are each, separately, hydrogen, methyl, or ethyl.

2. The composition of claim 1, wherein $R_1$ and $R_2$ groups are ethyl groups.

3. The composition of claim 1, wherein the salt is a monosodium salt of the phosphorothioate group.

4. A composition comprising (S)-ethyl 2-amino-5-(((R)-1-ethoxy-1-oxo-3-(phosphonothio)propan-2-ylamino)-5-oxopentanoate monosodium salt.

5. A method for protecting cells from the toxic effects of free radical generating therapies comprising:
a) providing a subject with a condition being treated with therapies that are toxic to normal cells and disease cells,
b) co-administering to said subject: a) said toxic therapy and, b) a therapeutic agent, that through metabolism in said subject, causes accumulation of a chemoprotectant compound in said normal cells at a higher concentration than in said disease cells, wherein the therapeutic agent is the compound of the formula of claim 1.

6. The method of claim 5, wherein said chemoprotectant compound comprises glutathione.

7. The method of claim 5, wherein said disease cells comprise cancer cells.

8. The method of claim 5, wherein said toxic therapy comprises administration of an anti-cancer chemotherapy.

9. The method of claim 5, wherein said toxic therapy comprises administration of radiation.

10. A pharmaceutical formulation comprising the composition of claim 1 and a pharmaceutically acceptable carrier.

11. A pharmaceutical formulation comprising the composition of claim 4 and a pharmaceutically acceptable carrier.

12. A compound corresponding to the formula:

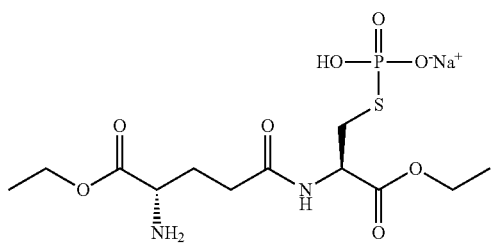

or a pharmaceutically acceptable salt thereof.

13. A composition comprising the compound of Formula I:

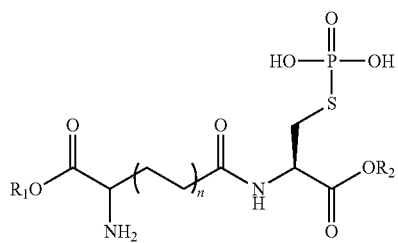

or salts thereof, wherein:

$R_1$ and $R_2$ are each, separately, hydrogen, methyl, or ethyl; and n is an integer from 2 to 10.

14. The composition of claim 13, wherein $R_1$ and $R_2$ groups are ethyl groups.

15. The composition of claim 13, wherein n is 2.

16. The composition of claim 13, wherein $R_1$ and $R_2$ groups are ethyl groups and wherein n is 2.

17. A method for protecting cells from the toxic effects of free radical generating therapies comprising:

a) providing a subject with a condition being treated with therapies that are toxic to normal cells and disease cells, b) co-administering to said subject: a) said toxic therapy and, b) a therapeutic agent, that through metabolism in said subject, causes accumulation of a chemoprotectant compound in said normal cells at a higher concentration than in said disease cells, wherein the therapeutic agent is the compound of the formula of claim 13.

18. The compound of claim 1, comprising a pharmaceutically acceptable salt.

* * * * *

UNITED STATES PATENT AND TRADEMARK OFFICE
CERTIFICATE OF CORRECTION

PATENT NO.        : 8,435,956 B2
APPLICATION NO.   : 13/469984
DATED             : May 7, 2013
INVENTOR(S)       : James P. Thomas Page 1 of 1

It is certified that error appears in the above-identified patent and that said Letters Patent is hereby corrected as shown below:

IN THE CLAIMS

Claim 4, Column 32, line 40 "$(((R)$" should read $((R)$

Signed and Sealed this
Second Day of July, 2013

Teresa Stanek Rea
*Acting Director of the United States Patent and Trademark Office*